United States Patent
Sahoo et al.

(10) Patent No.: US 7,319,170 B2
(45) Date of Patent: Jan. 15, 2008

(54) N-CYCLOHEXYLAMINOCARBONYL BENZENSULFONMIDE DERIVATIVES

(75) Inventors: Soumya P. Sahoo, Old Bridge, NJ (US); Hiroo Koyama, Hoboken, NJ (US); Daniel J. Miller, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 279 days.

(21) Appl. No.: 10/542,287

(22) PCT Filed: Jan. 13, 2004

(86) PCT No.: PCT/US2004/000689

§ 371 (c)(1),
(2), (4) Date: Jul. 15, 2005

(87) PCT Pub. No.: WO2004/066963

PCT Pub. Date: Aug. 12, 2004

(65) Prior Publication Data

US 2006/0111585 A1    May 25, 2006

Related U.S. Application Data

(60) Provisional application No. 60/440,761, filed on Jan. 17, 2003.

(51) Int. Cl.
*C07C 311/16*    (2006.01)
*C07C 311/19*    (2006.01)
*C07C 313/06*    (2006.01)
*A61K 31/64*    (2006.01)

(52) U.S. Cl. .......................... 564/43; 564/39; 564/42; 514/592

(58) Field of Classification Search ............. 564/39, 564/42, 43
See application file for complete search history.

(56) References Cited

U.S. PATENT DOCUMENTS 5,981,595 A    11/1999    Picard et al.

OTHER PUBLICATIONS

Database CAPLUS on STN, Acc. No. 1963:448120, BE 620808 (Jan. 30, 1963) (abstract).*

* cited by examiner

*Primary Examiner*—Brian Davis
(74) *Attorney, Agent, or Firm*—Richard C. Billups; Catherine D. Fitch; James L. McGinnis

(57) ABSTRACT

A class of N-cyclohexylaminocarbonyl benzenesulfonamide derivatives are agonists or partial agonists or antagonists of PPAR gamma and are useful in the treatment and control of hyperglycemia that is symptomatic of type II diabetes, as well as dyslipidemia, hyperlipidemia, hypercholesterolemia, hypertriglyceridemia, and obesity that are often associated with type 2 diabetes.

17 Claims, No Drawings

N-CYCLOHEXYLAMINOCARBONYL BENZENSULFONMIDE DERIVATIVES

CROSS REFERENCE TO RELATED APPLICATIONS

This application is a U.S. National Phase application under 35 U.S.C. § 371 of PCT Application No. PCT/US2004/000689, filed Jan. 13, 2004, which claims priority under 35 U.S.C. § 119(e) from U.S. Provisional Application Ser. No. 60/440,761, filed Jan. 17, 2003.

FIELD OF THE INVENTION

The instant invention is concerned with N-cyclohexylaminocarbonyl benzenesulfonamide derivatives which are useful as therapeutic compounds, particularly in the treatment of Type 2 diabetes mellitus, and of conditions that are often associated with this disease, including obesity and lipid disorders.

BACKGROUND OF THE INVENTION

Diabetes is a disease derived from multiple causative factors and is characterized by elevated levels of plasma glucose (hyperglycemia) in the fasting state or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin-dependent diabetes mellitus (NIDDM), insulin is still produced in the body. Patients having type 2 diabetes often have hyperinsulinemia (elevated plasma insulin levels); however, these patients are insulin resistant, which means that they have a resistance to the effect of insulin in stimulating glucose and lipid metabolism in the main insulin-sensitive tissues, which are muscle, liver and adipose tissues. Patients who are insulin resistant but not diabetic compensate for the insulin resistance by secreting more insulin, so that serum glucose levels are not elevated enough to meet the criteria of Type 2 diabetes. In patients with Type 2 diabetes, even elevated plasma insulin levels are insufficient to overcome the pronounced insulin resistance.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Many patients who have insulin resistance or Type 2 diabetes often have several symptoms that together are referred to as syndrome X, or the metabolic syndrome. A patient having this syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome, whether or not they have or develop overt diabetes mellitus, have an increased risk of developing the macrovascular and microvascular complications that are listed above that occur with type 2 diabetes, such as atherosclerosis and coronary heart disease.

Insulin resistance is not primarily caused by a diminished number of insulin receptors but by a post-insulin receptor binding defect that is not yet completely understood. This lack of responsiveness to insulin results in insufficient insulin-mediated activation of uptake, oxidation and storage of glucose in muscle and inadequate insulin-mediated repression of lipolysis in adipose tissue and of glucose production and secretion in the liver.

There are several available treatments for type 2 diabetes, each of which has its own limitations and potential risks. Physical exercise and a reduction in dietary intake of calories often dramatically improve the diabetic condition and are the best first line treatment of type 2 diabetes. Compliance with this treatment is very poor because of well-entrenched sedentary lifestyles and excess food consumption, especially of foods containing high amounts of fat. A widely used drug treatment involves the administration of meglitinide or a sulfonylurea (e.g. tolbutamide or glipizide), which are insulin secretagogues. These drugs increase the plasma level of insulin by stimulating the pancreatic β-cells to secrete more insulin. When administration of a sulfonylurea or meglitinide becomes ineffective, the amount of insulin in the body can be supplemented by the injection of insulin so that insulin concentrations are high enough to stimulate even the very insulin-resistant tissues. However, dangerously low levels of plasma glucose can result from administration of insulin and/or insulin secretagogues, and an increased level of insulin resistance due to the even higher plasma insulin levels can occur.

The biguanides are another class of drugs that are widely used to treat type 2 diabetes. The two best known biguanides, phenformin and metformin, cause some correction of hyperglycemia without risk of causing hypoglycemia. The biguanides can be used either with insulin or with an insulin secretagogue without increasing the risk of hypoglycemia. However, phenformin and metformin can induce lactic acidosis and nausea/diarrhea. Metformin has a lower risk of side effects than phenformin and is widely prescribed for the treatment of Type 2 diabetes.

The glitazones (i.e. 5-benzylthiazolidine-2,4-diones) are a newer class of compounds that can ameliorate hyperglycemia and other symptoms of type 2 diabetes. These agents substantially increase insulin sensitivity in muscle, liver and adipose tissue in several animal models of type 2 diabetes, resulting in partial or complete correction of elevated plasma glucose levels without the occurrence of hypoglycemia. The glitazones that are currently marketed (rosiglitazone and pioglitazone) are agonists of the peroxisome proliferator activated receptor (PPAR) gamma subtype. PPAR-gamma agonism is generally believed to be responsible for the improved insulin sensititization that is observed with the glitazones. New PPAR agonists are being developed for the treatment of Type 2 diabetes and/or dyslipidemia. Many of the newer PPAR compounds are agonists of one or more of the PPAR alpha, gamma and delta subtypes. Compounds that are agonists of both the PPAR alpha and PPAR gamma subtypes (PPAR alpha/gamma dual agonists) are promising because they reduce hyperglycemia and also improve lipid metabolism.

PPAR agonists, and particularly glitazones, have had shortcomings which have so far detracted from their attractiveness. Some of the compounds, and especially troglitazone, have exhibited liver toxicity. Troglitazone was eventually withdrawn from the marketplace because of hepatotoxicity. Another weakness in the currently marketed PPAR agonists is that monotherapy for type 2 diabetes produces only modest efficacy—a reduction in average plasma glucose of ≈20% and a decline from ≈9.0% to ≈8.0% in HemoglobinA1C. The current compounds also do not greatly improve lipid metabolism, and may actually have a negative effect on the lipid profile. These shortcomings have provided an incentive to develop better insulin sensitizers for Type 2 diabetes which function via similar mechanism(s) of action.

Recently, there have been reports of compounds that are PPAR gamma antagonists or partial agonists. WO01/30343 describes a specific compound that is a PPAR partial agonist/antagonist that is useful for the treatment of obesity and Type 2 diabetes. WO02/08188 discloses a class of PPAR agonists and partial agonists that are indole derivatives and that are useful in the treatment of Type 2 diabetes, with reduced side effects relating to body and heart weight gain.

SUMMARY OF THE INVENTION

The class of compounds described herein is a new class of PPAR agonists that do not contain a 1,3-thiazolidinedione moiety. The class of compounds includes many compounds that are PPARγ partial agonists, but also may include PPARγ full agonists and/or PPARγ antagonists. Some compounds may also have PPARα activity in addition to or instead of PPARγ activity. Some compounds may be mixed full or partial PPARα/γ agonists. Some compounds in this class of compounds may also have PPARδ activity. These compounds are useful in the treatment and control of diabetes, hyperglycemia, and insulin resistance.

The compounds may also be useful in the treatment of one or more lipid disorders, including mixed or diabetic dyslipidemia, isolated hypercholesterolemia, which may be manifested by elevations in LDL-C and/or non-HDL-C, hyper-apoBliproteinemia, hypertriglyceridemia, an increase in triglyceride-rich-lipoproteins, and low HDL cholesterol concentrations. They may also be useful in the treatment or amelioration of atherosclerosis, obesity, vascular restenosis, inflammatory conditions, psoriasis, polycystic ovary syndrome, and other PPAR mediated diseases, disorders and conditions.

The present invention provides compounds having the structure of Formula I, including pharmaceutically acceptable salts and prodrugs of these compounds:

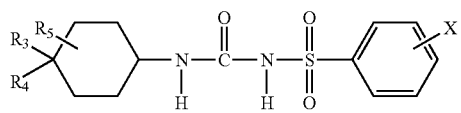

I

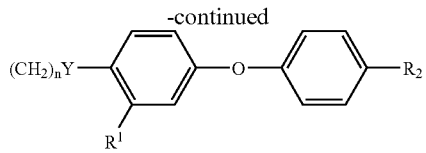

-continued

The substituent groups in Formula I are defined in the next section.

The compounds of this invention may be effective in lowering glucose, lipids, and insulin in diabetic patients and in improving insulin resistance in non-diabetic patients that have impaired glucose tolerance and/or are in a pre-diabetic condition, thereby reducing the risk that the patient will develop diabetes. The compounds are expected to be efficacious in the treatment of non-insulin dependent diabetes mellitus (NIDDM) in human and mammalian patients and in the treatment and control of conditions associated with NIDDM, including hyperglycemia, hyperlipidemia, dyslipidemia, obesity, hypercholesterolemia, hypertrigyceridemia, atherosclerosis, vascular restenosis, inflammatory conditions, neoplastic conditions, and other PPAR mediated diseases, disorders and conditions.

DETAILED DESCRIPTION OF THE INVENTION

The invention has numerous embodiments, as summarized below. In the compounds of Formula I:

$R^1$ is selected from the group consisting of H, Cl, F, and $C_{1-4}$alkyl, where $C_{1-4}$alkyl is optionally substituted with 1-3 halogen atoms independently selected from F and Cl. In preferred groups of compounds, $R^1$ is $C_{2-3}$ alkyl, which is optionally substituted with 1-3 F atoms. In other preferred groups of compounds, $R^1$ is n-propyl.

$R^2$ is selected from the group consisting of H, Cl, F, $C_{1-4}$alkyl, $OC_{1-4}$alkyl, and $—S(O)_2CH_3$, where $C_{1-4}$alkyl and $OC_{1-4}$alkyl are optionally substituted with 1-3 halogen atoms independently selected from F and Cl. In preferred groups of compounds, $R^2$ is selected from H, F, $—OC_{1-3}$ alkyl, and $—S(O)_2CH_3$, where $—OC_{1-3}$ alkyl is optionally substituted with 1-3 F atoms. In other preferred compounds, $R^2$ is $—OCH_2CH_3$ or $—OCH_2CF_3$.

$R^3$, $R^4$ and $R^5$ are independently selected from the group consisting of hydrogen, F, Cl, $C_{1-3}$alkyl, and $—OC_{1-3}$alkyl, where $C_{1-3}$alkyl and $—OC_{1-3}$alkyl are optionally substituted with 1-3 halogens independently selected from F and Cl. In preferred groups of compounds, $R^5$ is H and $R^3$ and $R^4$ are each independently selected from H, F, $CH_3$, $CF_3$, $—OCH_3$, $—OCF_3$, $—OCH_2CH_3$ and $—OCH_2CF_3$. In other preferred groups of compounds, $R^3$ and $R^4$ are H, and R5 is selected from the group consisting of H, F, $CH_3$, $CF_3$, $—OCH_3$, $—OCF_3$, $—OCH_2CH_3$ and $—OCH_2CF_3$.

In other preferred groups of compounds, $R^1$ is selected from Cl and n-propyl; $R^2$ is selected from H and F; and $R^3$, $R^4$ and $R^5$ are H.

X and Y are each independently selected from the group consisting of O, S, SO, and $SO_2$. In preferred groups of compounds, X and Y are each independently selected from O and S. In other preferred groups of compounds, X and Y are each O. The group X is optionally attached to the phenyl of the N-cyclohexylaminocarbonyl benzenesulfonamide moiety at the position that is meta or para to the sulfonamide group. In many preferred sub-groups of compounds, X is attached to the position that is para to the sulfonamide group.

The letter n represents an integer selected from 1, 2, 3, and 4. In preferred sub-groups of compounds, n may be 3 or 4. In other sub-groups of compounds, n is 1-3. In still other groups of compounds, n is 3.

In many of the preferred compounds, X and Y are O; n is an integer selected from 1-3; $R^3$, $R^4$ and $R^5$ are H; $R^1$ is selected from n-propyl and Cl; and $R^2$ is selected from H, F, and $-S(O)_2CH_3$.

Specific embodiments of compounds of this invention are provided in the Examples and in the tables that are appended hereto.

The compounds as defined above may be used to treat the following diseases, as well as other diseases not listed below:

(1) a method for treating non-insulin dependent diabetes mellitus (type 2 diabetes) in a mammalian or human patient in need of such treatment which comprises administering to the patient a therapeutically effective amount of a compound of Formula I;

(2) a method for treating or controlling hyperglycemia in a mammalian or human patient in need of such treatment which comprises administering to the patient a therapeutically effective amount of a compound of Formula I;

(3) a method for treating or controlling the metabolic syndrome in a mammalian or human patient in need of such treatment which comprises administering to the patient a therapeutically effective amount of a compound of Formula I;

(4) a method for treating or controlling obesity in a mammalian or human patient in need of such treatment which comprises administering to the patient a therapeutically effective amount of a compound of Formula I;

(5) a method for treating or controlling hypercholesterolemia in a mammalian or human patient in need of such treatment which comprises administering to the patient a therapeutically effective amount of a compound of Formula I;

(6) a method for treating or controlling hypertriglyceridemia in a mammalian or human patient in need of such treatment which comprises administering to the patient a therapeutically effective amount of a compound of Formula I;

(7) a method for treating or controlling one or more lipid disorders, including mixed or diabetic dyslipidemia, low HDL cholesterol, high LDL cholesterol, hyperlipidemia, hypercholesterolemia, and hypertriglyceridemia in a mammalian or human patient in need of such treatment which comprises administering to the patient a therapeutically effective amount of a compound of Formula I;

(8) a method for reducing the risks of adverse sequelae associated with metabolic syndrome in a mammalian or human patient in need of such treatment which comprises administering to the patient a therapeutically effective amount of a compound of Formula I; and (9) a method for treating atherosclerosis and for reducing the risks and/or delaying the onset of sequelae in a mammalian or human patient in need of such treatment or at risk of developing atherosclerosis or sequelae of atherosclerosis, which comprises administering to the patient a therapeutically effective amount of a compound of Formula I. Sequelae of atherosclerosis include for example angina, claudication, heart attack, stroke, etc.

Definitions

"Ac" is acetyl, which is $CH_3C(O)-$.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Cycloalkyl" means mono- or bicyclic saturated carbocyclic rings, each having from 3 to 10 carbon atoms, unless otherwise stated. The term also includes a monocyclic ring fused to an aryl group. Examples of cycloalkyl include cyclopropyl, cyclopentyl, cyclohexyl, cycloheptyl, and the like.

"Halogen" includes fluorine, chlorine, bromine and iodine.

"Me" represents methyl.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Optical Isomers—Diastereomers—Geometric Isomers—Tautomers

Compounds of Formula I may contain one or more asymmetric centers and can thus occur as racemates, racemic mixtures, single enantiomers, diastereomeric mixtures and individual diastereomers. The present invention is meant to comprehend all such isomeric forms of the compounds of Formula I.

Some of the compounds described herein may contain olefinic double bonds, and unless specified otherwise, are meant to include both E and Z geometric isomers.

Some of the compounds described herein may exist with different points of attachment of hydrogen, referred to as tautomers. An example is a ketone and its enol form, known as keto-enol tautomers. The individual tautomers as well as mixtures thereof are encompassed with compounds of Formula I.

Compounds of the Formula I having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

Prodrugs, which are chemical entities that are converted to the claimed chemical entities of this invention as they are being administered to a patient or after they have been administered to a patient, are also compounds of this invention. The metabolites of these prodrugs, where the metabolites are compounds having Formula I, are also compounds of this invention, regardless of how they have been delivered into the patient.

Utilities

Compounds of the present invention are potent ligands having agonist, partial agonist or antagonist activity on one or more of the various peroxisome proliferator activated receptor subtypes, particularly PPARγ. The compounds may also be ligands or agonists, partial agonists or antagonists of the PPARα subtype as well as the PPARγ, resulting in mixed PPARα/γ agonism or in agonism of mainly the PPARα subtype. Some compounds may also be PPARδ ligands and have PPARδ activity. The compounds of this invention are useful in treating or controlling diseases, disorders or conditions which are mediated by one or more ligands of the individual PPAR subtypes (eg. γ or α) or a combination of PPAR subtypes (e.g. α/γ). One aspect of the present invention provides a method for-the treatment and control of such diseases, disorders, or conditions in a mammal which comprises administering to such mammal a therapeutically effective amount of a compound of Formula I. Compounds of the present invention may be useful in treating or controlling many PPAR mediated diseases and conditions, including, but not limited to, (1) diabetes mellitus, and especially non-insulin dependent diabetes mellitus (NIDDM), (2) hyperglycemia, (3) low glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) irritable bowel syndrome, (16) inflammatory bowel disease, including Crohn's disease and ulcerative colitis, (17) other inflammatory conditions, (18) pancreatitis, (19) abdominal obesity, (20) neurodegenerative disease, (21) retinopathy, (22) psoriasis, (23) metabolic syndrome, (24) ovarian hyperandrogenism (polycystic ovarian syndrome), and other diseases or disorders where insulin resistance is a component. They may also have utility in treating high blood pressure, neoplastic conditions, adipose cell tumors, adipose cell carcinomas, such as liposarcoma, prostate cancer and other cancers, including gastric, breast, bladder and colon cancers, angiogenesis, and Alzheimer's disease.

The compounds may also have utility in treating osteoporosis. The compounds of this invention may treat osteoporosis or reduce the risk of developing osteoporosis by slowing or stopping the loss of bone density in a patient who has osteoporosis or is at risk of developing osteoporosis. The compounds of this invention may also reverse the loss of bone mass in patients who have already begun to lose bone mass.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound having formula I. The compound may be used alone or advantageously may be administered with a cholesterol biosynthesis inhibitor, particularly an HMG-CoA reductase inhibitor such as lovastatin, simvastatin, pravastatin, fluvastatin, atorvastatin, rivastatin, itavastatin, or ZD4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), niacin, bile acid sequestrants, microsomal triglyceride transport inhibitors, and bile acid reuptake inhibitors. These combination treatments may also be effective for the treatment or control of one or more related conditions selected from the group consisting of hypercholesterolemia, atherosclerosis, hyperlipidemia, hypertriglyceridemia, dyslipidemia, high LDL, and low HDL.

Another aspect of the invention provides a method of treating inflammatory conditions, including inflammatory bowel disease, Crohn's disease, and ulcerative colitis by administering an effective amount of a compound of this invention to a patient in need of treatment. Additional inflammatory diseases that may be treated with the instant invention include gout, rheumatoid arthritis, osteoarthritis, multiple sclerosis, asthma, ARDS, psoriasis, vasculitis, ischemia/reperfusion injury, frostbite, and related diseases.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus and/or hyperglycemia or hypertriglyceridemia or other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 1 milligram to about 350 milligrams. This dosage regimen may be adjusted within this range or outside of this range to provide the optimal therapeutic response.

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt or prodrug thereof as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) (i) other PPAR agonists such as the glitazones (e.g. troglitazone, pioglitazone, englitazone, MCC-555, rosiglitazone, and the like), and compounds disclosed in WO97/27857, 97/28115, 97/28137 and 97/27847; (ii) biguanides such as metformin and phenformin; (iii) protein tyrosine phosphatase-1B (PTP-1B) inhibitors, and (iv) dipeptidyl peptidase IV (DP-IV) inhibitors;

(b) insulin or insulin mimetics;

(c) sulfonylureas such as tolbutamide and glipizide, or related materials;

(d) α-glucosidase inhibitors (such as acarbose);

(e) cholesterol lowering agents such as (i) HMG-CoA reductase inhibitors (lovastatin, simvastatin, rosuvastatin, pravastatin, fluvastatin, atorvastatin, rivastatin, itavastatin, ZD4522 and other statins), (ii) bile acid sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as KRP-297, (vi) inhibitors of cholesterol absorption, such as for example beta-sitosterol, (vii) acyl CoA:cholesterol acyltransferase inhibitors, such as for example ezetemibe and avasimibe, and (viii) phenolic anti-oxidants, such as probucol;

(f) PPARδ agonists such as those disclosed in WO97/28149;

(g) antiobesity compounds such as fenfluramine, dexfenfluramine, phentiramine, sulbitramine, orlistat, neuropeptide Y5 inhibitors, and $\beta_3$ adrenergic receptor agonists;

(h) an ileal bile acid transporter inhibitor;

(i) agents intended for use in inflammatory conditions such as aspirin, non-steroidal anti-inflammatory drugs, glucocorticoids, azulfidine, and cyclo-oxygenase 2 selective inhibitors;

(j) glucagon receptor antagonists;

(k) GLP-1, GIP-1, and GLP-1 analogs, such as exendins.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, other PPAR agonists, PTP-1B inhibitors, DP-IV inhibitors, and anti-obesity compounds.

Biological Assays

A) PPAR Binding Assays

For preparation of recombinant human PPARγ, PPARδ, and PPARα: Human PPARγ$_2$, human PPARγ and human PPARα were expressed as gst-fusion proteins in *E. coli*. The full length human cDNA for PPARγ$_2$ was subcloned into the pGEX-2T expression vector (Pharmacia). The full length human cDNAs for PPARδ and PPARα were subcloned into the pGEX-KT expression vector (Pharmacia). *E. coli* containing the respective plasmids were propagated, induced, and harvested by centrifugation. The resuspended pellet was broken in a French press and debris was removed by centrifugation at 12,000×g. Recombinant human PPAR receptors were purified by affinity chromatography on glutathione sepharose. After application to the column, and one wash, receptor was eluted with glutathione. Glycerol (10%) was added to stabilize the receptor and aliquots were stored at −80° C. For binding to PPARγ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 10 nM [$^3$H$_2$] AD5075, (21 Ci/mmole), ± test compound as described in Berger et al (Novel peroxisome proliferator-activated receptor (PPARγ) and PPARδ ligands produce distinct biological effects. J. Biol. Chem. (1999), 274: 6718-6725. Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARδ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 2.5 nM [$^3$H$_2$]L783483, (17 Ci/mmole), ± test compound as described in Berger et al (Novel peroxisome proliferator-activated receptorγ (PPARγ) and PPARδ ligands produce distinct biological effects. 1999 J Biol Chem 274: 6718-6725). (L-783483 is 3-chloro-4-(3-(7-propyl-3-trifluoromethyl-6-benz-[4,5]-isoxazoloxy)propylthio)phenylacetic acid, Ex. 20 in WO 97/28137). Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARα, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 5.0 nM [$^3$H$_2$]L-797773, (34 Ci/mmole), ± test compound. (L-797733 is (3-(4-(3-phenyl-7-propyl-6-benz-[4,5]-isoxazoloxy)butyloxy))phenylacetic acid, Ex.62 in WO 97/28137). Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

B) Gal-4 hPPAR Transactivation Assays

The chimeric receptor expression constructs, pcDNA3-hPPARγ/GAL4, pcDNA3-hPPARδ/GAL4, pcDNA3-hPPARα/GAL4 were prepared by inserting the yeast GAL4 transcription factor DBD adjacent to the ligand binding domains (LBDs) of hPPARγ, hPPARδ, hPPARα, respectively. The reporter construct, pUAS(5×)-tk-luc was generated by inserting 5 copies of the GAIA response element upstream of the herpes virus minimal thymidine kinase promoter and the luciferase reporter gene. pCMV-lacZ contains the galactosidase Z gene under the regulation of the cytomegalovirus promoter. COS-1 cells were seeded at $12 \times 10^3$ cells/well in 96 well cell culture plates in high glucose Dulbecco's modified Eagle medium (DMEM) containing 10% charcoal stripped fetal calf serum (Gemini Bio-Products, Calabasas, Calif.), nonessential amino acids, 100 units/ml Penicillin G and 100 mg/ml Streptomycin sulfate at 37° C. in a humidified atmosphere of 10% CO$_2$. After 24 h, transfections were performed with Lipofectamine (GIBCO BRL, Gaithersburg, Md.) according to the instructions of the manufacturer. Briefly, transfection mixes for each well contained 0.48 μl of Lipofectamine, 0.00075 μg of pcDNA3-PPAR/GAL4 expression vector, 0.045 μg of pUAS(5×)-tk-luc reporter vector and 0.0002 μg of pCMV-lacZ as an internal control for transactivation efficiency. Cells were incubated in the transfection mixture for 5 h at 37° C. in an atmosphere of 10% $CO_2$ The cells were then incubated for ~48 h in fresh high glucose DMBM containing 5% charcoal stripped fetal calf serum, nonessential amino acids, 100 units/ml Penicillin G and 100 mg/ml Streptomycin sulfate ± increasing concentrations of test compound. Since the compounds were solubilized in DMSO, control cells were incubated with equivalent concentrations of DMSO; final DMSO concentrations were ≦0.1%, a concentration which was shown not to effect transactivation activity. Cell lysates were produced using Reporter Lysis Buffer (Promega, Madison, Wis.) according to the manufacturer's instructions. Luciferase activity in cell extracts was determined using Luciferase Assay Buffer (Promega, Madison, Wis.) in an ML3000 luminometer (Dynatech Laboratories, Chantilly, Va.). β-galactosidase activity was determined using β-D-galactopyranoside (Calbiochem, San Diego, Calif.).

Agonism is determined by comparison of maximal transactivation activity with standard PPAR agonists, such as rosiglitazone and pioglitazone. Generally, if the maximal stimulation of transactivation is less than 50% of the effect observed with rosiglitazone, then the compound is designated as a partial agonist. If the maximal stimulation of transactivation is greater than 50% of the effect observed with rosiglitazone, then the compound is designated as a full agonist.

C) In Vivo Studies

Male db/db mice (10-11 week old C57Bl/KFJ, Jackson Labs, Bar Harbor, Me.) were housed 5/cage and allowed ad lib. access to ground Purina rodent chow and water. The animals, and their food, were weighed every 2 days and were dosed daily by gavage with vehicle (0.5% carboxymethylcellulose)±test compound at the indicated dose. Drug suspensions were prepared daily. Plasma glucose, and triglyceride concentrations were determined from blood obtained by tail bleeds at 3-5 day intervals during the study period. Glucose, and triglyceride, determinations were performed on a Boehringer Mannheim Hitachi 911 automatic analyzer (Boehringer Mannheim, Indianapolis, Ind.) using heparinized plasma diluted 1:6 (v/v) with normal saline. Lean animals were age-matched heterozygous mice maintained in the same manner.

EXAMPLES

The following Examples are provided to illustrate the invention and are not to be construed as limiting the invention in any manner. The scope of the invention is defined by the appended claims.

Example 1

N-[(cyclohexylamino)carbonyl]-4-[3-(4-phenoxy-2-propylphenoxy)propoxy]benzenesulfonamide

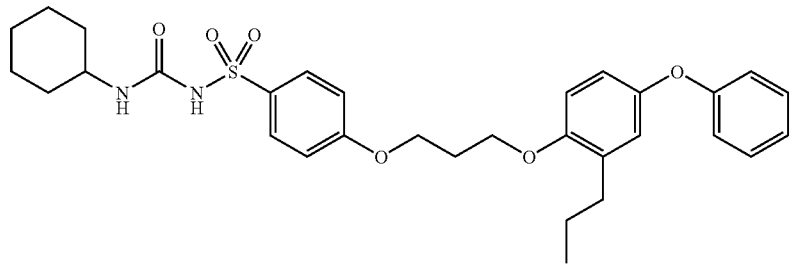

Step A: Preparation of 1-(3-bromopropoxy)4-phenoxy-2-propylbenzene

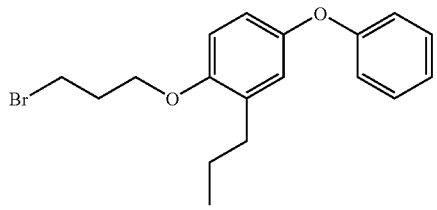

The title compound was prepared according to the method described in U.S. Pat. No. 6,008,237, Example 11, Step A.

Step B: Preparation of 4-[3-(4-phenoxy-2-propylphenoxy) propoxy]benzenesulfonamide

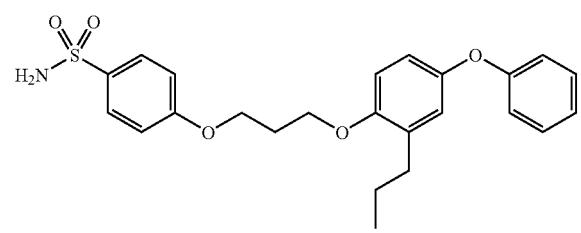

To a solution of 1-(3-bromopropoxy)-4-phenoxy-2-propylbenzene (1.01 g, 2.9 mmol) and 4-hydroxybenzenesulfonamide (0.5 g, 2.9 mmol) in dry DMF (29 mL) was added cesium carbonate (1.04 g, 3.2 mmol). The resulting suspension was stirred in a 50° C. oil bath for 5 h. After cooling to room temperature, the reaction suspension was concentrated under vacuum to a residue, which was then partitioned between ethyl acetate and water. The ethyl acetate phase was dried over sodium sulfate, filtered, and concentrated to an oil. The oil was chromatographed over silica gel with hexanes/ethyl acetate (2:1) to isolate the title compound., Step C: Preparation of N-[(cyclohexylamino)carbonyl]-4-[3-(4-phenoxy-2-propylphenoxy)propoxy]benzenesulfonamide To a solution of 4-[3-(4-phenoxy-2-propyl phenoxy)propoxy]benzenesulfonamide (0.045 g, 0.102 mmol) and acetone (3 mL) was added potassium carbonate (0.028 g, 0.204 mmol). To the resulting suspension was added cyclohexyl isocyanate (0.026 mL, 0.204 mmol) dropwise. The reaction suspension was then stirred in a 65° C. oil bath for 6 h. After cooling to room temperature, the reaction was concentrated to a residue. The residue was partitioned between ethyl acetate and water. The ethyl acetate phase was dried over sodium sulfate, filtered, and concentrated to an oil. The oil was chromatographed over silica gel with hexanes/ethyl acetate (4:1) and hexanes/ethyl acetate (3:1) to obtain the title compound.

1H NMR (500 MHz, CDCl$_3$): δ7.85 (d, 2H, J=8.9 Hz), 7.28 (m, 2H), 7.07 (t, 1H), 7.01 (d, 2H, J=8.9 Hz), 6.92 (dd, 2H, J=8.7, 0.9 Hz), 6.85 (s, 1H), 6.85 (s, 2H), 6.4 (d, 1H, J=7.8 Hz), 4.27 (t, 2H, J=6.1 Hz), 4.16 (t, 2H, J=6.1 Hz), 3.6 (m, 1H), 2.57 (t, 2H, J=7.5 Hz), 2.33 (quint, 2H, J=6.1 Hz), 1.85 (d, 2H, J=9.2 Hz), 1.7 (m, 4H), 1.6 (hex, 2H, J=7.5 Hz), 1.1-1.4 (m, 5H), 0.92 (t, 3H, J=7.5 Hz). MS: m/e=567 (M+1).

Example 2

N-[(cyclohexylamino)carbonyl]-3-[3-(4-phenoxy-2-propylphenoxy)propoxy]benzenesulfonamide

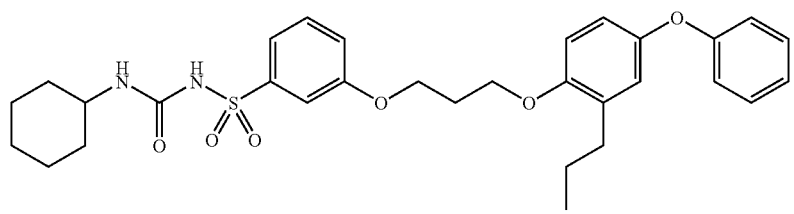

Step A: Preparation of 3-hydroxybenzenesulfonamide

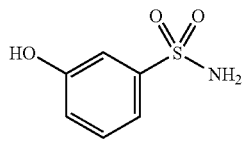

To a solution of 3-aminobenzenesulfonamide (2.35 g, 13.6 mmol) in 30% sulfuric acid (18 mL) stirred in a 0° C. ice-water bath was added dropwise a solution of sodium nitrite (1.22 g, 17.7 mmol) in water (10 mL). The resulting reaction solution continued to stir in an ice-water bath for 30 min. The solution was then stirred in a 100° C. oil bath for 30 min. After cooling to room temperature, the reaction solution was partitioned between ethyl acetate and brine. After shaking, the aqueous phase was extracted with ethyl acetate. The combined ethyl acetate phases were dried over sodium sulfate, filtered, and concentrated to a yellow solid (2.11 g, 89% yield).

Step B: Preparation of 1-(3-bromopropoxy)-4-phenoxy-2-propylbenzene

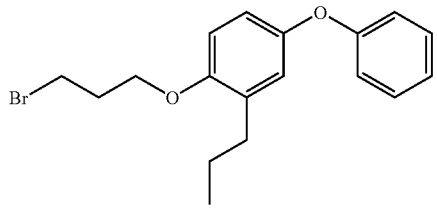

The title compound was prepared according to the method described in U.S. Pat. No. 6,008,237 Example 11, Step A.

Step C: Preparation of 3-[3-(4-phenoxy-2-propylphenoxy)propoxy]benzenesulfonamide

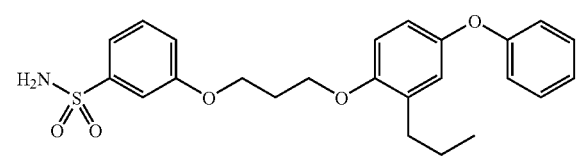

A solution of 3-hydroxybenzenesulfonamide (0.5 g, 2.89 mmol) and 1-(3-bromopropoxy)-4-phenoxy-2-propylbenzene (1.01 g, 2.89 mmol) with cesium carbonate (1.04 g, 3.18 mmol) in dry DMF (10 mL) was stirred at 50° C. for 5 h. The reaction suspension was cooled to room temperature and concentrated under vacuum to an orange residue. The residue was partitioned between ethyl acetate and water. The ethyl acetate phase was dried over sodium sulfate, filtered, and concentrated to an oil. The oil was chromatographed over silica gel with hexanes/ethyl acetate (2:1) to provide the title compound.

Step D: Preparation of N-[(cyclohexylamino)carbonyl]-3-[3-(4-phenoxy-2-propylphenoxy)propoxy]benzenesulfonamide To a solution of 3-[3-(4-phenoxy-2-propyl phenoxy)propoxy]benzenesulfonamide (0.04 g, 0.0906 mmol) and acetone (3 mL) was added potassium carbonate (0.025 g, 0.181 mmol). To the resulting suspension was added cyclohexyl isocyanate (0.023 mL, 0.181 mmol) dropwise. The reaction suspension was then stirred in a 65° C. oil bath for 5 h. After cooling to room temperature, the reaction was concentrated to a residue. The residue was partitioned between ethyl acetate and water. The ethyl acetate phase was dried over sodium sulfate, filtered, and concentrated to an oil. The oil was chromatographed over silica gel with hexanes/ethyl acetate (4:1) and hexanes/ethyl acetate (3:1) to afford the title compound.

1H NMR (500 MHz, CDCl$_3$): δ7.49-7.44 (m, 2H), 7.41 (s, 1H), 7.3 (m, 2H), 7.19 (d, 1H, J=7.1 Hz), 7.05 (t, 1H), 6.95

(dd, 2H, J=8.7, 0.9 Hz), 6.87 (s, 1H), 6.83 (s, 2H), 6.47 (d, 1H, J=7.8 Hz), 4.25 (t, 2H, J=6.1 Hz), 4.15 (t, 2H, J=6.1 Hz), 3.65 (m, 1H), 2.58 (t, 2H, J=7.5 Hz), 2.33 (quint, 2H, J=6.1 Hz), 1.85 (d, 2H, J=9.2 Hz), 1.7 (m, 4H), 1.58 (hex, 2H, J=7.5 Hz), 1.1-1.4 (m, 5H), 0.92 (t, 3H, J=7.5 Hz). MS: m/e=567 (M+1).

Examples 3-9

The compounds written below as Examples 3-9 were made using the methodology that was described in Examples 1 and 2, starting with chemical compounds that are readily made or readily available. The syntheses are readily accomplished by one of ordinary skill in the art.

Ex 3

N-[(cyclohexylamino)carbonyl]-4-{3-[4-(4-fluorophenoxy)-2-propylphenoxy]propoxy}benzenesulfonamide

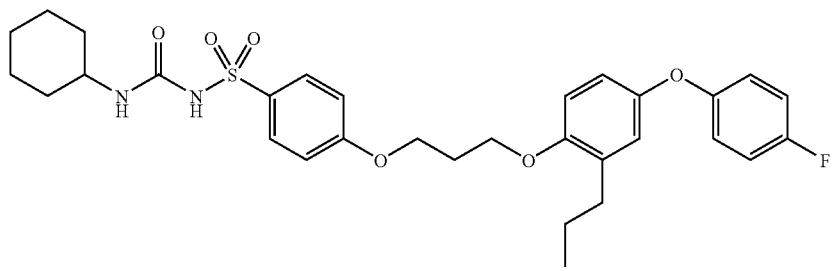

Ex 4

4-{3-[2-chloro-4-(4-fluorophenoxy)phenoxy]propoxy}-N-[(cyclohexylamino)carbonyl]benzenesulfonamide

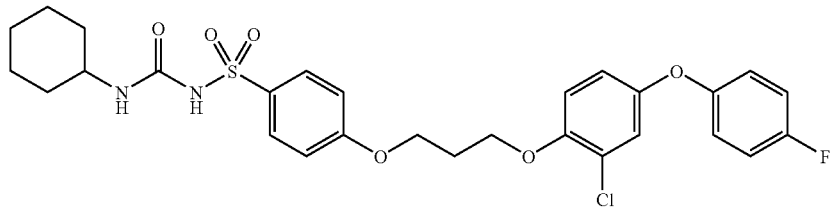

Ex 5

N-[(cyclohexylamino)carbonyl]-4-(3-{4-[4-(methylsulfonyl)phenoxy]-2-propylphenoxy}propoxy)benzenesulfonamide

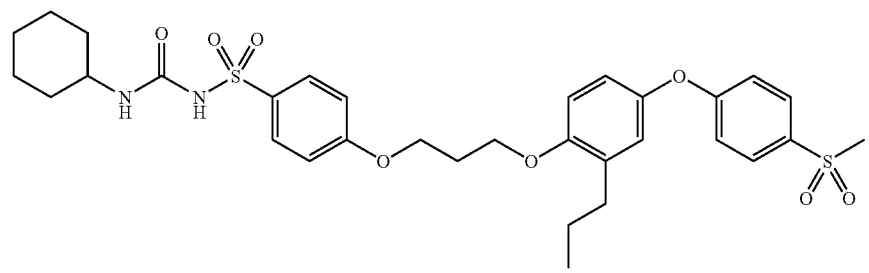

Example 6

N-[(cyclohexylamino)carbonyl]-4-[3-(4-phenoxyphenoxy)propoxy]benzenesulfonamide

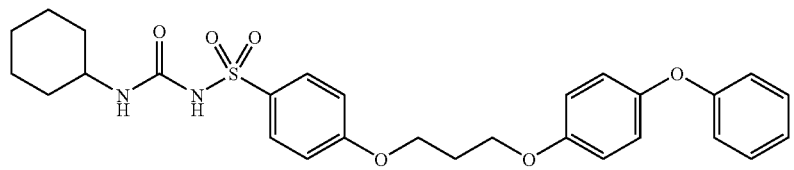

Example 7

3-{3-[2-chloro-4-(4-fluorophenoxy)phenoxy]propoxy}-N-[(cyclohexylamino)carbonyl]benzenesulfonamide

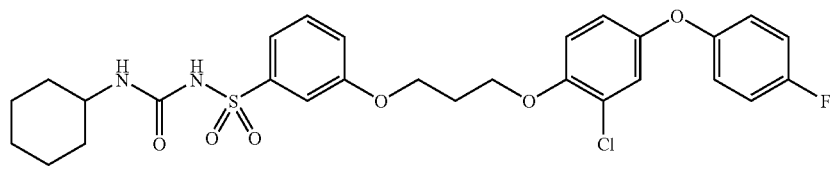

Example 8

N-[(cyclohexylamino)carbonyl]-3-{3-[4-(4-fluorophenoxy)-2-propylphenoxy]propoxy}benzenesulfonamide

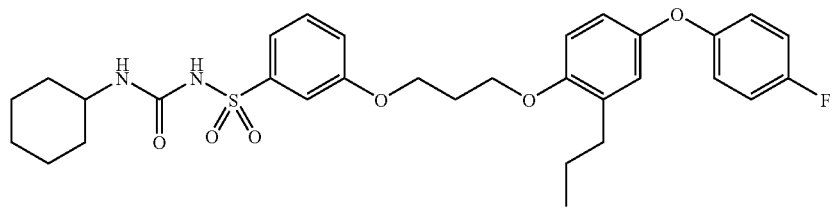

Example 9

N-[(cyclohexylamino)carbonyl]-3-[4-(4-phenoxy-2-propylphenoxy)butoxy]benzenesulfonam

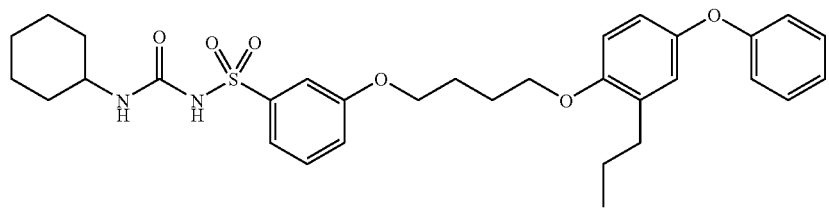

What is claimed is:

1. A compound of Formula I:

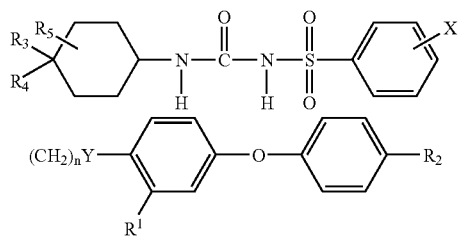

or a pharmaceutically acceptable salt thereof, wherein:
R$^1$ is selected from the group consisting of H, Cl, F, and C$_{1-4}$alkyl, where C$_{1-4}$alkyl is optionally substituted with 1-3 halogen atoms independently selected from F and Cl;
R$^2$ is selected from the group consisting of H, Cl, F, C$_{1-4}$alkyl, OC$_{1-4}$alkyl, and —S(O)$_2$CH$_3$, where C$_{1-4}$alkyl and OC$_{1-4}$alkyl are optionally substituted with 1-3 halogen atoms independently selected from F and Cl;
R$^3$, R$^4$ and R$^5$ are independently selected from the group consisting of hydrogen, F, Cl, C$_{1-3}$alkyl, and —OC$_{1-3}$alkyl, where C$_{1-3}$alkyl and —OC$_{1-3}$alkyl are optionally substituted with 1-3 halogens independently selected from F and Cl;
X and Y are each independently selected from the group consisting of O, S, SO, and SO$_2$; and
n represents an integer selected from 1, 2, 3, and 4.

2. The compound according to claim 1 wherein R$^2$ is selected from H, F, —OC$_{1-3}$ alkyl, and —S(O)$_2$CH$_3$, where —OC$_{1-3}$ alkyl is optionally substituted with 1-3 F atoms.

3. The compound according to claim 1, wherein
R$^1$ is selected from Cl and n-propyl;
R$^2$ is selected from H and F; and
R$^3$, R$^4$ and R$^5$ are H.

4. The compound according to claim 1, wherein R$^2$ is —OCH$_2$CH$_3$ or —OCH$_2$CF$_3$.

5. The compound according to claim 1, wherein R$^5$ is H; and R$^3$ and R$^4$ are each independently selected from H, F, CH$_3$, CF$_3$, —OCH$_3$, —OCF$_3$, —OCH$_2$CH$_3$ and —OCH$_2$CF$_3$.

6. The compound according to claim 1, wherein X and Y are each independently selected from O and S.

7. The compound according to claim 1, wherein X and Y are each O.

8. The compound according to claim 1, wherein the group X is attached to the phenyl of the N-cyclohexylaminocarbonyl benzenesulfonamide moiety at the position that is meta to the sulfonamide group.

9. The compound according to claim 1, wherein the group X is attached to the phenyl of the N-cyclohexylaminocarbonyl benzenesulfonamide moiety at the position that is para to the sulfonamide group.

10. The compound according to claim 1, wherein n is 1-3.

11. The compound according to claim 1, wherein n is 3 or 4.

12. The compound according to claim 1, wherein X and Y are O; n is an integer selected from 1-3; R$^3$, R$^4$ and R$^5$ are H; R$^1$ is selected from n-propyl and Cl; and R$^2$ is selected from H, F, and —S(O)$_2$CH$_3$.

13. The compound according to claim 1, wherein R$^1$ is C$_{2-3}$ alkyl, which is optionally substituted with 1-3 F atoms.

14. The compound according to claim 1, wherein R$^1$ is n-propyl.

15. The compound which is selected from the compounds below, or a pharmaceutically acceptable salt thereof:

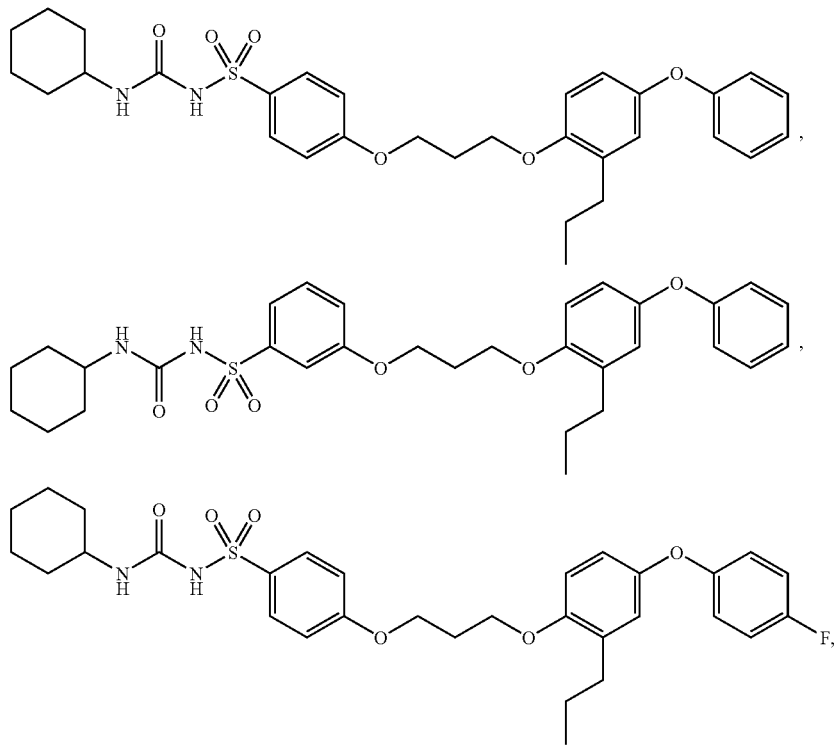

-continued
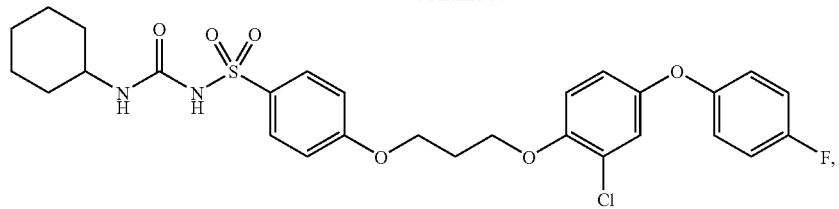
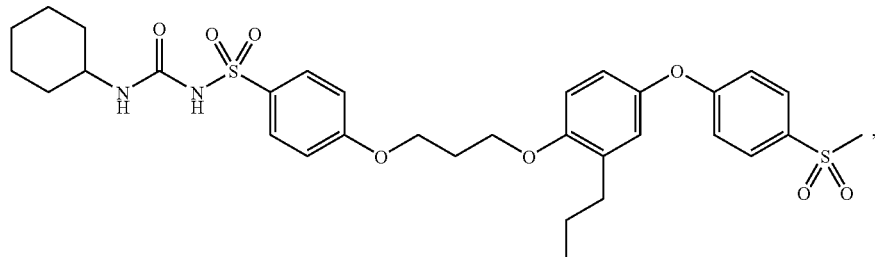
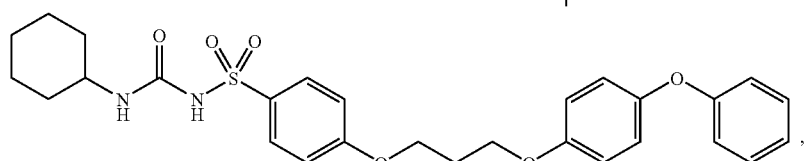
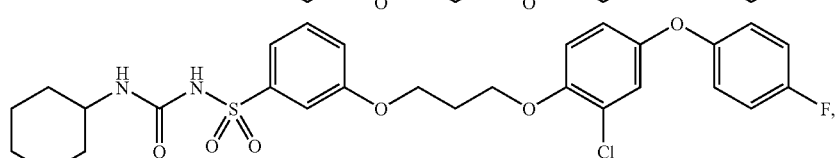
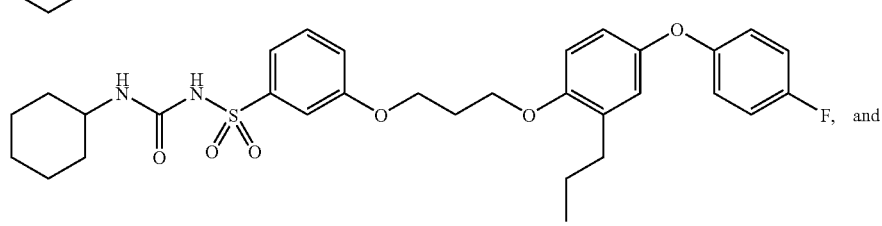
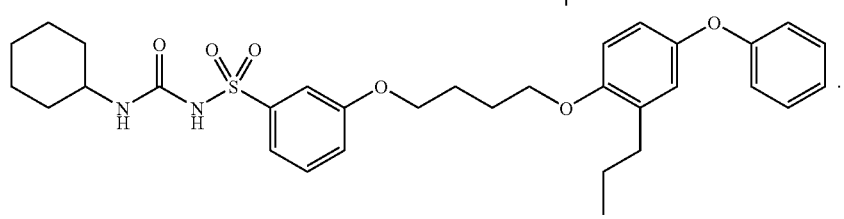
16. A pharmaceutical composition comprising a compound of claim 1 and a pharmaceutically acceptable carrier.
17. A method for treating hyperglycemia in a mammalian or human patient having non-insulin dependent (Type 2) diabetes mellitus which comprises administering to said patient a therapeutically effective amount of a compound of claim 1.
* * * * *

UNITED STATES PATENT AND TRADEMARK OFFICE
CERTIFICATE OF CORRECTION

PATENT NO. : 7,319,170 B2 Page 1 of 1
APPLICATION NO. : 10/542287
DATED : January 15, 2008
INVENTOR(S) : Souyma P. Sahoo, Hiroo Koyama and Daniel J. Miller It is certified that error appears in the above-identified patent and that said Letters Patent is hereby corrected as shown below:

On the front page, the title should be changed to the following:

(54) N-CYCLOHEXYLAMINOCARBONYL BENZENESULFONAMIDE DERIVATIVES

Signed and Sealed this

Fifth Day of August, 2008

JON W. DUDAS
*Director of the United States Patent and Trademark Office*

UNITED STATES PATENT AND TRADEMARK OFFICE
CERTIFICATE OF CORRECTION

PATENT NO. : 7,319,170 B2  Page 1 of 1
APPLICATION NO. : 10/542287
DATED : January 15, 2008
INVENTOR(S) : Souyma P. Sahoo, Hiroo Koyama and Daniel J. Miller It is certified that error appears in the above-identified patent and that said Letters Patent is hereby corrected as shown below:

On the front page, and Column 1, lines 1 and 2 the title should be changed to the following:

(54) N-CYCLOHEXYLAMINOCARBONYL BENZENESULFONAMIDE DERIVATIVES

This certificate supersedes the Certificate of Correction issued August 5, 2008.

Signed and Sealed this

Twenty-sixth Day of August, 2008

JON W. DUDAS
*Director of the United States Patent and Trademark Office*